(12) United States Patent
Cho et al.

(10) Patent No.: US 8,691,492 B2
(45) Date of Patent: Apr. 8, 2014

(54) SILANE-BASED COMPOUNDS AND PHOTOSENSITIVE RESIN COMPOSITION COMPRISING THE SAME

(75) Inventors: Changho Cho, Anseong-si (KR); Yoon Hee Heo, Daejeon (KR); Sunghyun Kim, Daejeon (KR); Han Soo Kim, Daejeon (KR); Sunhwa Kim, Daejeon (KR); Won Jin Chung, Daejeon (KR)

(73) Assignee: LG Chem, Ltd., Seoul (KR)

( * ) Notice: Subject to any disclaimer, the term of this patent is extended or adjusted under 35 U.S.C. 154(b) by 48 days.

(21) Appl. No.: 13/566,434

(22) Filed: Aug. 3, 2012

(65) Prior Publication Data

US 2013/0034814 A1 Feb. 7, 2013

(30) Foreign Application Priority Data

Aug. 4, 2011 (KR) .................. 10-2011-0077769

(51) Int. Cl.
*G03C 1/00* (2006.01)
*G03F 7/00* (2006.01)

(52) U.S. Cl.
USPC .................. 430/270.1; 430/7; 430/281.1

(58) Field of Classification Search
USPC .................. 430/7, 270.1, 281.1; 556/423
See application file for complete search history.

(56) References Cited

U.S. PATENT DOCUMENTS

| 8,133,962 B2 * | 3/2012 | Kim et al. ............ 526/287 |
| 2012/0196949 A1 * | 8/2012 | Heo et al. ............ 522/63 |
| 2012/0208930 A1 * | 8/2012 | Kim et al. ............ 523/456 |
| 2013/0030077 A1 * | 1/2013 | Kim et al. ............ 522/79 |

* cited by examiner

*Primary Examiner* — Stewart Fraser
(74) *Attorney, Agent, or Firm* — Rothwell, Figg, Ernst & Manbeck, P.C.

(57) ABSTRACT

The present application relates to a new silane-based compound, a photosensitive resin composition including the same, and a photosensitive material including the same. The photosensitive resin composition including the silane-based compound according to the exemplary embodiment of the present application increases adhesion strength to a substrate, such that a developing property is excellent and there are no surface stains or defects during a subsequent process. Accordingly, a photosensitive material, a color filter and the like having excellent quality may be manufactured by using the photosensitive resin composition according to the exemplary embodiment of the present application.

18 Claims, No Drawings

SILANE-BASED COMPOUNDS AND PHOTOSENSITIVE RESIN COMPOSITION COMPRISING THE SAME

CROSS-REFERENCE TO RELATED APPLICATIONS

This application claims priority to and the benefit of Korean Patent Application No. 10-2011-0077769 filed in the Korean Intellectual Property Office on Aug. 4, 2011, the entire contents of which are incorporated herein by reference.

TECHNICAL FIELD

The present application relates to a new silane-based compound, a photosensitive resin composition including the same, a photosensitive material manufactured by using the same, and an electronic device manufactured by using the same.

BACKGROUND ART

A photosensitive resin composition may be used to form a pattern by forming a coat by applying the photosensitive resin composition on a substrate, performing exposure on a predetermined portion of the coat by using a photomask and the like by light radiation, and removing a non-exposure portion by developing treatment.

Since the photosensitive resin composition can be cured by irradiating light, the photosensitive resin composition is used for photocurable ink, a photosensitive printed board, various photoresists, a color filter photoresist for LCD, a photoresist for resin black matrixes, a transparent photosensitive material or the like.

The photosensitive resin composition generally includes an alkali-soluble resin, a polymerizable compound having an ethylenically unsaturated bond, a photopolymerization initiator, and a solvent.

In the photosensitive resin composition, an improvement in developing property, such as a reduction in developing time or an improvement in sensitivity, is an important issue in terms of an improvement in production efficiency.

In the related art, when the binder resin is manufactured, a method of adding an excessive amount of acid group monomer to increase a ratio of the acid group monomer in the binder resin is used. However, the binder resin having the high acid value has low solubility to a solvent typically used when a photopolymerizable functional group is introduced, thus, there is a problem in that precipitation occurs during polymerization not to allow a desired molecular weight to be obtained. Further, in the case where the ratio of the acid group monomer is high when the binder resin is manufactured, the ratio of the monomer providing other properties is relatively reduced to deteriorate other properties.

Accordingly, in the art, various studies need to be performed to improve a developing property of the photosensitive resin composition.

SUMMARY OF THE INVENTION

The present application has been made in an effort to provide a new silane-based compound increasing adhesion strength to a substrate to improve a developing property of a photosensitive resin composition, a photosensitive resin composition including the same, a photosensitive material manufactured by using the same, and an electronic device manufactured by using the same.

An exemplary embodiment of the present application provides a silane-based compound represented by the following Chemical Formula 1.

[Chemical Formula 1]

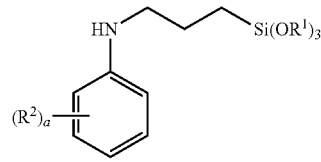

In Chemical Formula 1,
$R^1$ is an alkyl group having 1 to 5 carbon atoms,
$R^2$ is each independently a halogen group or $-C(R^2)_3$,
$R^3$ is a halogen group, and
a is 1 to 5.

Another exemplary embodiment of the present application provides a photosensitive resin composition including: the silane-based compound represented by Chemical Formula 1, a binder resin, a polymerizable compound including an ethylenically unsaturated bond, a photoactive compound, and a solvent.

Another exemplary embodiment of the present application provides a photosensitive material manufactured by using the photosensitive resin composition.

Another exemplary embodiment of the present application provides a color filter including the photosensitive material.

Another exemplary embodiment of the present application provides a method of manufacturing a photosensitive material, including: applying the photosensitive resin composition on a substrate; and exposing and developing the applied photosensitive resin composition.

Another exemplary embodiment of the present application provides an electronic device manufactured by using the photosensitive resin composition.

According to the exemplary embodiments of the present application, the photosensitive resin composition including the silane-based compound represented by Chemical Formula 1 increases adhesion strength to a substrate, such that a developing property is excellent and there are no surface stains or defects during a subsequent process. Accordingly, a photosensitive material, a color filter and the like having excellent quality may be manufactured by using the photosensitive resin composition.

DETAILED DESCRIPTION

Hereinafter, the present application will be described in detail.

A silane-based compound according to an exemplary embodiment of the present application is represented by the following Chemical Formula 1.

[Chemical Formula 1]

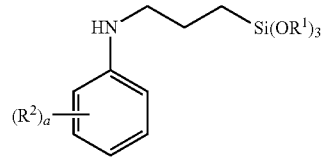

In Chemical Formula 1, $R^1$ may be an alkyl group having 1 to 5 carbon atoms, and specifically a methyl group or an ethyl group.

$R^2$ may be each independently a halogen group or $-C(R^2)_3$, and $R^3$ may be a halogen group. Specifically, $R^2$ may be F or $CF_3$.

a may be 1 to 5 and specifically 1 or 2.

In the silane-based compound according to the exemplary embodiment of the present application, substituent groups of Chemical Formula 1 will be described in more detail below.

An alkyl group may be a straight chain or a branched chain, and specific examples thereof include a methyl group, an ethyl group, a propyl group, an isopropyl group, a butyl group, a t-butyl group and the like, but are not limited thereto.

The halogen group may be F, Cl, Br, or I.

The silane-based compound of Chemical Formula 1 may be more preferably a compound represented by any one of Chemical Formulas 2 to 9 of the following Table 1.

TABLE 1

Chemical Formula 2

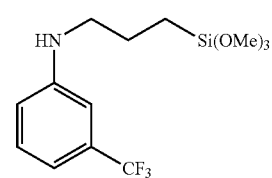

Chemical Formula 3

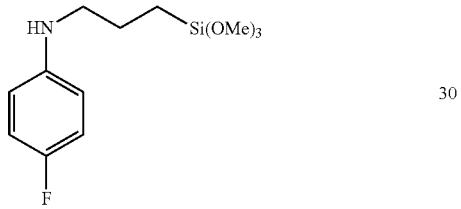

Chemical Formula 4

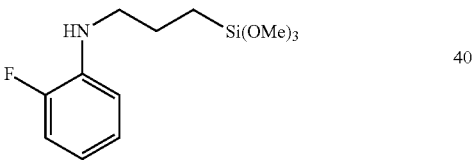

Chemical Formula 5

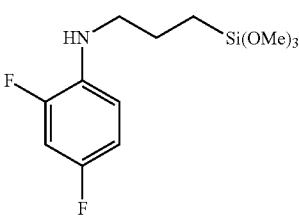

TABLE 1-continued

Chemical Formula 6

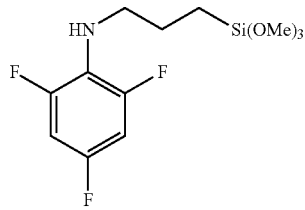

Chemical Formula 7

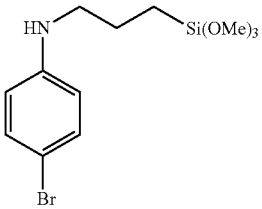

Chemical Formula 8

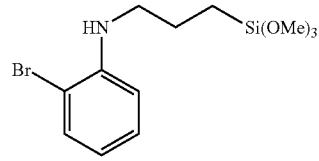

Chemical Formula 9

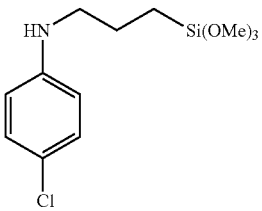

The photosensitive resin composition according to the exemplary embodiment of the present application includes the silane-based compound represented by Chemical Formula 1, a binder resin, a polymerizable compound including an ethylenically unsaturated bond, a photoactive compound, and a solvent.

In the photosensitive resin composition according to the exemplary embodiment of the present application, the silane-based compound represented by Chemical Formula 1 acts as an adhesion aid improving adhesion strength to a substrate.

In the related art, a silane-based compound having the following Structural Formula is mainly used as the adhesion aid in the photosensitive resin composition.

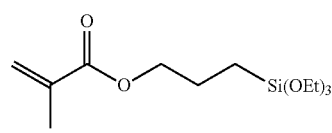

However, in the exemplary embodiment of the present application, the silane-based compound represented by Chemical Formula 1 is included as the adhesion aid in the photosensitive resin composition to increase the adhesion strength to the substrate, such that a developing property is excellent and there are no surface stains or defects during a subsequent process. Accordingly, a photosensitive material, a color filter and the like having excellent quality may be manufactured by using the photosensitive resin composition.

It is preferable that the content of the silane-based compound represented by Chemical Formula 1 be 0.01 to 5 wt % based on the total weight of the photosensitive resin composition.

In the photosensitive resin composition according to the exemplary embodiment of the present application, a detailed description of constituent components other than the silane-based compound represented by Chemical Formula 1 is as follows.

In the photosensitive resin composition according to the exemplary embodiment of the present application, the binder resin is an alkali-soluble resin, and may employ a copolymerization resin of a monomer for providing mechanical strength and a monomer for providing alkali solubility.

Examples of the monomer that can contribute to mechanical strength of the film may include one kind or more and preferably two kinds or more selected from the group consisting of one kind or more unsaturated ester carboxylates selected from the group consisting of benzyl(metha)acrylate, methyl(metha)acrylate, ethyl(metha)acrylate, butyl(metha)acrylate, dimethylaminoethyl(metha)acrylate, isobutyl (metha)acrylate, t-butyl(metha)acrylate, cyclohexyl(metha)acrylate, isobonyl(metha)acrylate, ethylhexyl(metha)acrylate, 2-phenoxyethyl(metha)acrylate, tetrahydrofurfuryl (metha)acrylate, hydroxyethyl(metha)acrylate, 2-hydroxypropyl(metha)acrylate, 2-hydroxy-3-chloropropyl (metha)acrylate, 4-hydroxybutyl(metha)acrylate, acyloctyloxy-2-hydroxypropyl(metha)acrylate, glycerol(metha)acrylate, 2-methoxyethyl(metha)acrylate, 3-methoxybutyl (metha)acrylate, ethoxydiethyleneglycol(metha)acrylate, methoxytriethyleneglycol(metha)acrylate, methoxytripropyleneglycol(metha)acrylate, poly(ethylene glycol)methylether(metha)acrylate, phenoxydiethyleneglycol(metha)acrylate, p-nonylphenoxypolyethyleneglycol(metha)acrylate, p-nonylphenoxypolypropyleneglycol(metha)acrylate, glycidyl(metha)acrylate, tetrafluoropropyl(metha)acrylate, 1,1, 1,3,3,3-hexafluoroisopropyl(metha)acrylate, octafluoropentyl(metha)acrylate, heptadecafluorodecyl(metha)acrylate, tribromophenyl(metha)acrylate, dicyclopentanyl(metha) acrylate, dicyclopentenyl(metha)acrylate, dicyclopentenyloxyethylacrylate, isobonylmethacrylate, adamentylmethacrylate, methyl α-hydroxymethyl acrylate, ethyl α-hydroxymethyl acrylate, propyl α-hydroxymethyl acrylate, and butyl α-hydroxymethyl acrylate;

aromatic vinyls selected from the group consisting of styrene, α-methylstyrene, (o,m,p)-vinyltoluene, (o,m,p)-methoxystyrene, and (o,m,p)-chlorostyrene;

unsaturated ethers selected from the group consisting of vinyl methyl ether, vinyl ethyl ether, and allyl glycidyl ether;

unsaturated imides selected from the group consisting of N-phenyl maleimide, N-(4-chlorophenyl) maleimide, N-(4-hydroxyphenyl) maleimide, and N-cyclohexyl maleimide; and one kind and preferably two kinds or more maleic anhydrides selected from the group consisting of maleic anhydride and methylmaleic anhydride, but are not limited thereto.

Further, preferable examples of the monomer for providing alkali solubility include one kind or more selected from the group consisting of a (metha)acrylic acid, a crotonic acid, an itaconic acid, a maleic acid, a fumaric acid, a monomethyl maleic acid, a 5-nobonen-2-carboxylic acid, mono-2-((metha)acryloyloxy)ethyl phthalate, mono-2-((metha)acryloyloxy)ethyl succinate, and ω-carboxypolycaprolactone mono(metha)acrylate, but are not limited thereto.

In addition, the binder resin represented by the following Chemical Formula 10 as well as the monomers may be used.

[Chemical Formula 10]

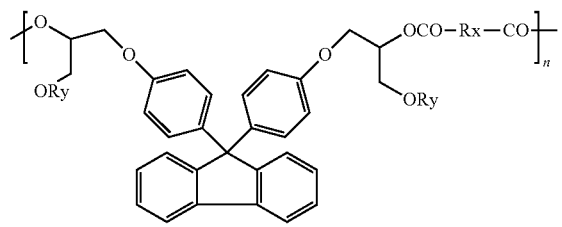

In Chemical Formula 10, Rx is a structure that forms a bond by addition reacting 5-membered cyclic carboxylic anhydride or diisocyanate, Ry is selected from hydrogen, acryloyl, and methaacryloyl, and n is 3 to 8.

Examples of specific compounds of carboxylic anhydride constituting Rx include one kind or more selected from the group consisting of succinic anhydride, methylsuccinic anhydride, 2,2-dimethylsuccinic anhydride, isobutenylsuccinic anhydride, 1,2-cyclohexanedicarboxylic anhydride, hexahydro-4-methylphthalic anhydride, itaconic anhydride, tetrahydrophthalic anhydride, 5-norbornene-2,3-dicarboxylic anhydride, methel-5-norbornene-2,3-dicarboxylic anhydride, 1,2, 3,4-cyclobutanetetracarboxylic dianhydride, maleic anhydride, citraconic anhydride, 2,3,-dimethylmaleic anhydride, 1-cyclopentene-1,2-dicarboxylic dianhydride, 3,4,5,6-tetrahydrophthalic anhydride, phthalic anhydride, bisphthalic anhydride, 4-methylphthalic anhydride, 3,6-dichlorophthalic anhydride, 3-hydrophthalic anhydride, 1,2, 4-benzenetricarboxylic anhydride, 4-nitrophthalic anhydride, and diethyleneglycol-1,2-bistrimellitic anhydride, but are not limited thereto.

Specific examples of diisocyanate constituting Rx include one kind or more selected from the group consisting of trimethylene diisocyanate, tetramethylene diisocyanate, hexamethylene diisocyanate, pentamethylene diisocyanate, 1,2-propylene diisocyanate, 2,3-butylene diisocyanate, 1,3-butylene diisocyanate, dodecamethylene diisocyanate, 2,4,4-trimethyl hexamethylene diisocyanate, w,w'-diisocyanate-1, 3-dimethylbenzene, w,w'-diisocyanate-1,4-dimethylbenzene, w,w'-diisocyanate-1,3-diethylbenzene, 1,4-tetramethylxylene diisocyanate, 1,3-tetramethylxylene diisocyanate, isophorone diisocyanate, 1,3-cyclopentane diisocyanate, 1,3-cyclohexane diisocyanate, 1,4-cyclohexane diisocyanate, methyl-2,4-cyclohexane diisocyanate, methyl-2,6-cyclohexane diisocyanate, 4,4'-methylene bisisocyanate methylcyclohexane, 2,5-isocyanatemethyl bicyclo [2,2,2]heptane, and 2,6-isocyanatemethyl bicyclo[2,2,1]heptane, but are not limited thereto.

The weight average molecular weight of the binder resin may be 1,000 to 50,000 g/mol and preferably 2,000 to 30,000 g/mol. In the case where the weight average molecular weight of the binder resin is 1,000 or more, heat resistance and chemical resistance are good, and in the case where the weight average molecular weight is 50,000 or less, there are effects that it is possible to prevent a problem of hindering developing because solubility to the developing solution is reduced and prevent a problem of hindering uniform coating due to excessively increase viscosity of the solution.

An acid value of the binder resin may be 30 to 300 KOH mg/g and preferably about 50 to 150 KOH mg/g. In the case where the acid value is 30 KOH mg/g or more, developing may be well performed to obtain a clean pattern, and in the case where the acid value is 300 KOH mg/g or less, there is effect that it is possible to prevent a problem of removal of the pattern because a washing property is excessively improved.

In the exemplary embodiment of the present application, the content of the binder resin is preferably 1 to 20 wt % based on the total weight of the photosensitive resin composition, but is not limited thereto. If the content of the binder resin is 1 wt % or more, there is an effect that patterning using the alkali aqueous solution is well performed, and it is possible to prevent a problem that it is difficult to form the pattern because solubility to the developing solution is not exhibited, and if the content of the binder resin is 20 wt % or less, there are effects that it is possible to prevent removal of the pattern during the developing process and prevent occurrence of a problem that it is difficult to perform coating due to excessively high viscosity of the entire solution.

In the photosensitive resin composition according to the exemplary embodiment of the present application, the polymerizable compound including the ethylenically unsaturated bond is a matter having an ethylenically unsaturated double bond and specifically at least one unsaturated group capable of performing addition polymerization in a molecule, and a compound having a boiling point of 100° C. or more or a functional monomer to which caprolactone is introduced may be used.

Examples of the compound having at least one unsaturated group capable of performing addition polymerization in the molecule and the boiling point of 100° C. or more may include one kind or more monofunctional monomers selected from the group consisting of polyethyleneglycol mono (metha)acrylate, polypropyleneglycol mono(metha)acrylate, and phenoxyethyl (metha)acrylate; or one kind or more polyfunctional monomers selected from the group consisting of polyethyleneglycol (metha)acrylate, polypropyleneglycol (metha)acrylate, trimethylolethane triacrylate, trimethylolpropane triacrylate, neopentylglycol (metha)acrylate, pentaerythritol tetraacrylate, pentaerythritol triacrylate, dipentaerythritol pentaacrylate, and dipentaerythritol hexaacrylate.

Further, examples of the polyfunctional monomer to which caprolactone is introduced may include KAYARAD DPCA-20, 30, 60, and 120 introduced to dipentaerythritol; KAYARAD TC-110S introduced to tetrahydrofuryl acrylate; and KAYARAD HX-220 and KAYARAD HK-620 introduced to neopentylglycol hydroxypyvalate and the like.

In addition to the aforementioned monomers, epoxy acrylate of a bisphenol A derivative, novolac-epoxy acrylate, and U-324A, U15HA, and U-4HA that are polyfunctional acrylate of urethanes and the like may be used, and the functional monomers having the ethylenically unsaturated double bond may be used alone or as a mixture of two kinds or more.

In the exemplary embodiment of the present application, it is preferable that the polymerizable compound including the ethylenically unsaturated bond be included in a content of 1 to 30 wt % (included in a content of 5 to 50 wt % based on the solid of the resin composition) based on the total weight of the photosensitive resin composition, if the content is 1 wt % or more, a crosslinking reaction is performed by light, which is preferable, and photosensitivity or strength of a coating film is not reduced, and if the content is 30 wt % or less, there are effects that it is possible to prevent a problem that it is difficult to form the pattern because solubility to alkali is reduced and a problem that strength of the film is not sufficient due to excessively high adhesion property of the photosensitive resin layer.

In the photosensitive resin composition according to the exemplary embodiment of the present application, the photoactive compound is a material that promotes crosslinking by generating a radical by light, and is also called a photoinitiator, and it is preferable to use one kind or more compounds selected from the group consisting of an acetophenone-based compound, a biimidazole-based compound, a triazine-based compound, and an oxime-based compound while mixing the compounds.

The acetophenone-based compound that can be used as the photoactive compound is selected from the group consisting of 2-hydroxy-2-methyl-1-phenylpropane-1-one, 1-(4-isopropylphenyl)-2-hydroxy-2-methylpropane-1-one, 4-(2-hydroxyethoxy)-phenyl-(2-hydroxy-2-propyl)ketone, 1-hydroxycyclohexylphenylketone, benzoinmethyl ether, benzomethyl ether, benzoinisobutyl ether, benzoinbutyl ether, 2,2-dimethoxy-2-phenylacetophenone, 2-methyl-(4-methylthio)phenyl-2-morpholino-1-propane-1-one, 2-benzyl-2-dimethylamino-1-(4-morpholinophenyl)-butane-1-one, 2-(4-bromo-benzyl-2-dimethylamino-1-(4-morpholinophenyl)-butane-1-one, and 2-methyl-1-[4-(methylthio)phenyl]-2-morpholinopropane-1-one, the biimidazole-based compound is selected from the group consisting of 2,2-bis(2-chlorophenyl)-4,4',5,5'-tetraphenyl biimidazole, 2,2'-bis(o-chlorophenyl)-4,4',5,5'-tetrakis(3,4,5-trimethoxyphenyl)-1,2'-biimidazole, 2,2'-bis(2,3-dichlorophenyl)-4,4',5,5'-tetraphenyl biimidazole, and 2,2'-bis(o-chlorophenyl)-4,4,5,5'-tetraphenyl-1,2'-biimidazole, the triazine-based compound is selected from the group consisting of 3-{4-[2,4-bis(trichloromethyl)-s-triazine-6-yl]phenylthio}propionic acid, 1,1,1,3,3,3-hexafluoroisopropyl-3-{4-[2,4-bis(trichloromethyl)-s-triazine-6-yl]phenylthio}propionate, ethyl-2-{4-[2,4-bis(trichloromethyl)-s-triazine-6-yl]phenylthio}acetate, 2-epoxyethyl-2-{4-[2,4-bis(trichloromethyl)-s-triazine-6-yl]phenylthio}acetate, cyclohexyl-2-{4-[2,4-bis(trichloromethyl)-s-triazine-6-yl]phenylthio}acetate, benzyl-2-{4-[2,4-bis(trichloromethyl)-s-triazine-6-yl]phenylthio}acetate, 3-{chloro-4-[2,4-bis(trichloromethyl)-s-triazine-6-yl]phenylthio}propionic acid, 3-{4-[2,4-bis(trichloromethyl)-s-triazine-6-yl]phenylthio}propionamide, 2,4-bis(trichloromethyl)-6-p-methoxystyryl-s-triazine, 2,4-bis(trichloromethyl)-6-(1-p-dimethylaminophenyl)-1,3,-butadienyl-s-triazine, and 2-trichloromethyl-4-amino-6-p-methoxystyryl-s-triazine, examples of the oxime-based compound include 1,2-octadione-1-(4-phenylthio)phenyl-2-(o-benzoyloxime) (Cibagei, Co., Ltd, CGI 124), ethanone-1-(9-ethyl)-6-(2-methylbenzoyl-3-yl)-1-(o-acetyloxime) (CGI 242) and the like.

In the exemplary embodiment of the present application, the content of the photoactive compound is preferably 0.1 to 5 wt % based on the total weight of the photosensitive resin composition, but is not limited thereto. If the content is 0.1 wt % or more, sufficient sensitivity may be provided, and if the content is 5 wt % or less, a problem that UV rays do not reach the bottom due to excessively high UV absorption may be prevented.

In addition, the photoactive compound may further include 0.01 to 10 parts by weight of a photocrosslinking sensitizer promoting generating of a radical, or 0.01 to 10 parts by weight of a curing promoter promoting curing based on 100 parts by weight of the photoactive compound as an auxiliary component thereof.

Examples of the photocrosslinking sensitizer may include a benzophenone-based compound such as benzophenone, 4,4-bis(dimethylamino)benzophenone, 4,4-bis(diethylamino)benzophenone, 2,4,6-trimethylaminobenzophenone, methyl-o-benzoyl benzoate, 3,3-dimethyl-4-methoxybenzophenone, and 3,3,4,4-tetra(t-butylperoxycarbonyl)benzophenone; a fluorenone-based compound such as 9-fluorenone, 2-chloro-9-fluorenone, and 2-methyl-9-fluorenone; a thioxanthone-based compound such as thioxanthone, 2,4-diethyl thioxanthone, 2-chloro thioxanthone, 1-chloro-4-propyloxy thioxanthone, isopropylthioxanthone, and diisopropylthioxanthone; a xanthone-based compound such as xanthone and 2-methylxanthone; an anthraquinone-based compound such as anthraquinone, 2-methyl anthraquinone, 2-ethyl anthraquinone, t-butyl anthraquinone, and 2,6-dichloro-9,10-anthraquinone; an acridine-based compound such as 9-phenylacridine, 1,7-bis(9-acridinyl)heptane, 1,5-bis(9-acridinylpentane), and 1,3-bis(9-acridinyl)propane; a dicarbonyl compound such as benzyl, 1,7,7-trimethyl-bicyclo[2,2,1]heptane-2,3-dion, and 9,10-phenanthrenequinone; a phosphine oxide-based compound such as 2,4,6-trimethylbenzoyl diphenylphosphine oxide and bis(2,6-dimethoxybenzoyl)-2,4,4-trimethylpentylphosphine oxide; a benzophenone-based compound such as methyl-4-(dimethylamino) benzoate, ethyl-4-(dimethylamino)benzoate, and 2-n-butoxyethyl-4-(dimethylamino)benzoate; an amino synergist such as 2,5-bis(4-diethylaminobenzal)cyclopentanone, 2,6-bis(4-diethylaminobenzal)cyclohexanone, and 2,6-bis(4-diethylaminobenzal)-4-methyl-cyclopentanone; a coumarin-based compound such as 3,3-carbonylvinyl-7-(diethylamino) coumarin, 3-(2-benzothiazolyl)-7-(diethylamino)coumarin, 3-benzoyl-7-(diethylamino)coumarin, 3-benzoyl-7-methoxy-coumarin, and 10,10-carbonylbis[1,1,7,7-tetramethyl-2,3,6,7-tetrahydro-1H,5H,11H-C1]-benzopyrano[6,7,8-ij]-quinolizine-11-on; a chalcone compound such as 4-diethylamino chalcone and 4-azidbenzalacetophenone; 2-benzoylmethylene, 3-methyl-b-naphthothiazoline or the like.

Further, examples of the curing promoter may include one kind or more selected from the group consisting of 2-mercaptobenzoimidazole, 2-mercaptobenzothiazol, 2-mercaptobenzooxazole, 2,5-dimercapto-1,3,4-thiadiazole, 2-mercapto-4,6-dimethylaminopyridine, pentaerythritol-tetrakis(3-mercaptopropionate), pentaerythritol-tris(3-mercaptopropionate), pentaerythritol-tetrakis(2-mercaptoacetate), pentaerythritol-tris(2-mercaptoacetate), trimethylolpropane-tris(2-mercaptoacetate), and trimethylolpropane-tris(3-mercaptopropionate).

In the photosensitive resin composition according to the exemplary embodiment of the present application, preferable examples of the solvent include one kind or more selected from the group consisting of acetone, methyl ethyl ketone, methyl isobutyl ketone, methylcellosolve, ethylcellosolve, tetrahydrofuran, 1,4-dioxane, ethyleneglycol dimethyl ether, ethyleneglycol diethyl ether, propyleneglycol dimethyl ether, propyleneglycol methylether acetate, propyleneglycol diethylether, diethyleneglycol dimethylether, diethyleneglycol diethylether, diethyleneglycol methyl ethyl ether, chloroform, methylene chloride, 1,2-dichloroethane, 1,1,1-trichloroethane, 1,1,2-trichloroethane, 1,1,2-trichloroethene, hexane, heptane, octane, cyclohexane, benzene, toluene, xylene, methanol, ethanol, isopropanol, propanol, butanol, t-butanol, 2-ethoxy propanol, 2-methoxy propanol, 3-methoxy butanol, cyclohexanone, cyclopentanone, propyleneglycol methyl ether acetate, propelenglycol ethylether acetate, 3-methoxybutyl acetate, ethyl 3-ethoxy propionate, ethylcellosolve acetate, methylcellosolve acetate, butyl acetate, dipropyleneglycol monomethyl ether and the like, but are not limited thereto, and a solvent known in the art may be used.

In the exemplary embodiment of the present application, the content of the solvent is preferably 40 to 95 wt % based on the total weight of the photosensitive resin composition, but is not limited thereto.

Further, the photosensitive resin composition according to the exemplary embodiment of the present application may further include one or two or more additives such as a colorant, a thermal polymerization inhibitor, a dispersing agent, an antioxidant, a UV absorbent, a leveling agent, a plasticizer, an adhesion promoter, a filler or a surfactant according to the purpose thereof.

One kind or more pigments, dyes, or mixtures thereof may be used as the colorant. Specifically, metal oxides such as carbon black, graphite, and titanium black may be used as a black pigment. Examples of the carbon black include Cisto 5HIISAF-HS, Cisto KH, Cisto 3HHAF-HS, Cisto NH, Cisto 3M, Cisto 300HAF-LS, Cisto 116HMMAF-HS, Cisto 116MAF, Cisto FMFEF-HS, Cisto SOFEF, Cisto VGPF, Cisto SVHSRF-HS, and Cisto SSRF (Donghae Carbon, Co., Ltd.); Diagram black II, Diagram black N339, Diagram black SH, Diagram black H, Diagram LH, Diagram HA, Diagram SF, Diagram N550M, Diagram M, Diagram E, Diagram G, Diagram R, Diagram N760M, Diagram LR, #2700, #2600, #2400, #2350, #2300, #2200, #1000, #980, #900, MCF88, #52, #50, #47, #45, #45L, #25, #CF9, #95, #3030, #3050, MA7, MA77, MA8, MA11, MA100, MA40, OIL7B, OIL9B, OIL11B, OIL30B, and OIL31B (Mitsubishi Chemical, Co., Ltd.); PRINTEX-U, PRINTEX-V, PRINTEX-140U, PRINTEX-140V, PRINTEX-95, PRINTEX-85, PRINTEX-75, PRINTEX-55, PRINTEX-45, PRINTEX-300, PRINTEX-35, PRINTEX-25, PRINTEX-200, PRINTEX-40, PRINTEX-30, PRINTEX-3, PRINTEX-A, SPECIAL BLACK-550, SPECIAL BLACK-350, SPECIAL BLACK-250, SPECIAL BLACK-100, and LAMP BLACK-101 (Degussa, Co., Ltd.); RAVEN-1100ULTRA, RAVEN-1080ULTRA, RAVEN-1060ULTRA, RAVEN-1040, RAVEN-1035, RAVEN-1020, RAVEN-1000, RAVEN-890H, RAVEN-890, RAVEN-880ULTRA, RAVEN-860ULTRA, RAVEN-850, RAVEN-820, RAVEN-790ULTRA, RAVEN-780ULTRA, RAVEN-760ULTRA, RAVEN-520, RAVEN-500, RAVEN-460, RAVEN-450, RAVEN-430ULTRA, RAVEN-420, RAVEN-410, RAVEN-2500ULTRA, RAVEN-2000, RAVEN-1500, RAVEN-1255, RAVEN-1250, RAVEN-1200, RAVEN-1190ULTRA, and RAVEN-1170 (Columbia Carbon, Co., Ltd.), mixtures thereof or the like. Further, examples of the colorant exhibiting a color include carmine 6B (C.I. 12490), phthalocyanine green (C.I. 74260), phthalocyanine blue (C.I. 74160), perylene black (BASF K0084. K0086), cyanine black, linol yellow (C.I. 21090), linol yellow GRO (C.I. 21090), benzidine yellow 4T-564D, victoria pure blue (C.I. 42595), C.I. PIGMENT RED 3, 23, 97, 108, 122, 139, 140, 141, 142, 143, 144, 149, 166, 168, 175, 177, 180, 185, 189, 190, 192, 202, 214, 215, 220, 221, 224, 230, 235, 242, 254, 255, 260, 262, 264, and 272; C.I. PIGMENT GREEN 7, 36; C.I. PIGMENT blue 15:1, 15:3, 15:4, 15:6, 16, 22, 28, 36, 60, and 64; C.I. PIGMENT yellow 13, 14, 35, 53, 83, 93, 95, 110, 120, 138, 139, 150, 151, 154, 175, 180, 181, 185, 194, and 213; C.I. PIGMENT VIOLET 15, 19, 23, 29, 32, and 37, and the like, and in addition to this, a white pigment, a fluorescent pigment or the like may be used. A material in which zinc is used as the central metal other than copper may be used as the phthalocyanine-based complex compound used as the pigment.

Examples of the adhesion promoter may further include one kind or more selected from the group consisting of vinyltrimethoxysilane, vinyltriethoxysilane, vinyltris(2-methoxyethoxy)-silane, N-(2-aminoethyl)-3-aminopropylmethyldimethoxysilane, N-(2-aminoethyl)-3-aminopropylmethyltrimethoxy silane, 3-aminopropyltriethoxysilane, 3-glycidoxypropyltriethoxysilane, 3-glycidoxypropylmethyldimethoxysilane, 2-(3,4-ethoxy cyclohexyl)ethyltrimethoxysilane, 3-chloropropyl methyldimethoxysilane, 3-chloropropyl trimethoxy silane, 3-methacryloxypropyltrimethoxysilane, and 3-mercaptopropyltrimethoxysilane, in addition to the compound represented by Chemical Formula 1.

Examples of the antioxidant may include 2,2-thiobis(4-methyl-6-t-butylphenol), 2,6-g,t-butylphenol or the like, and examples of the UV absorbing agent may include 2-(3-t-butyl-5-methyl-2-hydroxyphenyl)-5-chloro-benzotriazole, alkoxy benzophenone or the like.

Further, examples of the thermal polymerization inhibitor may include one kind or more selected from the group consisting of p-anisole, hydroquinone, pyrocatechol, t-butyl catechol, N-nitrosophenylhydroxyamine ammonium salt, N-nitrosophenylhydroxyamine aluminum salt, hydroquinone, p-methoxyphenol, di-t-butyl-p-cresol, pyrogarol, t-butylcatechol, benzoquinone, 4,4-thiobis(3-methyl-6-t-butylphenol), 2,2-methylenebis(4-methyl-6-t-butylphenol), 2-mercaptoimidazole, and phenothiazine, but are not limited thereto, and may include matters generally known in the art.

Examples of the dispersing agent may include polymer type, non-ionic, anionic, or cationic dispersing agents. Non-limiting examples of the dispersing agent may include polyalkyleneglycol and esters thereof, polyoxyalkylene polyvalent alcohols, esteralkylene oxide additions, alcoholalkylene oxide additions, ester sulfonate, sulfonates, ester carboxylates, carboxylates, alkylamide alkylene oxide additions, alkylamine and the like, one kind or a mixture of two kinds or more selected from the examples may be used, but the examples are not limited thereto.

Examples of the surfactant may include MCF 350SF, F-475, F-488, F-552 (hereinafter, DIC, Co., Ltd.) and the like, but are not limited thereto.

All compounds that can be included in a known photosensitive resin composition may be used as the leveling agent, the photosensitizer, the plasticizer, the filler or the like.

In addition to this, the photosensitive resin composition according to the exemplary embodiment of the present application may further include one kind or more secondary additives selected from the group consisting of a resin binder having functionality, a polyfunctional monomer, a radiation sensitive compound, and other additives.

In the exemplary embodiment of the present application, the content of the colorant is preferably 1 to 20 wt % based on the total weight of the photosensitive resin composition, and the contents of the other additives are each independently preferably 0.01 to 5 wt % based on the total weight of the photosensitive resin composition.

Further, the exemplary embodiment of the present application provides a photosensitive material including the photosensitive resin composition. The photosensitive material includes the photosensitive resin composition.

The photosensitive resin composition according to the exemplary embodiment of the present application is preferably used in a pigment dispersion type photosensitive material for manufacturing a color filter, for example, a pigment dispersion type photosensitive material for manufacturing a TFT LCD color filter, a photosensitive material for forming a black matrix, for example, a photosensitive material for forming a black matrix of a TFT LCD or organic light emitting diode, a photosensitive material for forming an overcoat layer, and a column spacer photosensitive material, and may be used in manufacturing a photosensitive material for a photocurable paint, photocurable ink, photocurable adhesive, a printed board, and a printed circuit board, and other transparent photosensitive materials and PDPs, and the purpose thereof is not particularly limited. Particularly, it is preferable that the photosensitive resin composition according to the exemplary embodiment of the present application be used in a photosensitive material for color filter or a photosensitive material for black matrix.

In addition, a method of manufacturing a photosensitive material according to the exemplary embodiment of the present application includes applying the photosensitive resin composition on a substrate, and exposing and developing the applied photosensitive resin composition.

In the method for manufacturing the photosensitive material according to the exemplary embodiment of the present application, the applying of the photosensitive resin composition on the substrate may be performed on the substrate by using, for example, a method that is known in the art. To be more specific, examples of the method for applying the photosensitive resin composition may include a spray method, a roll coating method, a spin coating method, a bar coating method, a slit coating method and the like, but are not limited thereto.

In this case, examples of the substrate may include metal, paper, glass, plastic, silicon, polycarbonate, polyester, aromatic polyamide, polyamideimide, polyimide and the like, and these substrates may be subjected to appropriate pretreatment such as chemical treatment by a silane coupling agent, plasma treatment, ion plating, sputtering, a vapor reaction method and vacuum deposition according to the purpose thereof. In addition, a thin film transistor for driving may be selectively mounted on the substrate, and a nitrated silicon film may be sputtered thereon.

In the method of manufacturing the photosensitive material according to the exemplary embodiment of the present application, in more specific reviewing of the exposing and developing of the applied photosensitive resin composition, UV may be radiated on the prebaked coat film through a predetermined pattern mask and an unnecessary portion may be removed by developing using an alkali aqueous solution to form the pattern. In this case, a dipping method, a shower method and the like may be applied as the developing method without a limitation. A developing time is generally about 30 to 180 sec. Examples of the developing solution may include alkali aqueous solutions of inorganic alkalis such as sodium hydroxide, potassium hydroxide, sodium silicate, sodium methsilicate and ammonia; primary amines such as ethylamine and N-propylamine; secondary amines such as diethylamine and di-n-propylamine; tertiary amines such as trimethylamine, methyldiethylamine and dimethylethylamine; tertiary alcoholamines such as dimethylethanolamine, methyldiethanolamine and triethanolamine; tertiary cycloamines such as pyrrole, piperidine, n-methylpiperidine, n-methylpyrrolidine, 1,8-diazabicyclo[5.4.0]-7-undecene, 1,5-diazabicyclo[4.3.0]-5-nonene; aromatic tertiary amines such as pyridine, coridine, lutidine and quinoline; and quaternary ammonium salts such as tetramethylammonium hydroxide and tetraethylammonium hydroxide as an alkali aqueous solution.

After the developing, water washing may be performed for about 30 to 90 sec, and drying may be performed with air or nitrogen to form the pattern. This pattern may be post-baked by using a heating device such as a hot plate and an oven to obtain a final photosensitive material pattern. In this case, it is preferable that heating be performed at 150 to 250° C. for 10 to 90 min for the post-baking condition.

Examples of the light source for curing the photosensitive resin composition include a mercury vapor arc, a carbon arc, and a Xe arc emitting light having a wavelength of 250 to 450 nm, but are not limited thereto.

Further, the exemplary embodiment of the present application provides a color filter including the photosensitive material. The color filter may be manufactured according to a general method known in the art, except that the photosensitive material according to the exemplary embodiment of the present application is included therein.

The exemplary embodiment of the present application provides an electronic device manufactured by using the photosensitive resin composition.

Hereinafter, preferable Examples will be described in order to help understanding of the present application. However, the following Examples are set forth to illustrate the present application, but the scope of the present application is not limited thereto. Further, only a portion of examples according to the exemplary embodiment of the present application is shown in the following Examples, but, substantially, even in the case where equivalents thereof are used, it is clear to the person with ordinary skill in the art that the same effect as the present application can be exhibited.

Synthetic Example 1

Manufacturing of Compound 1

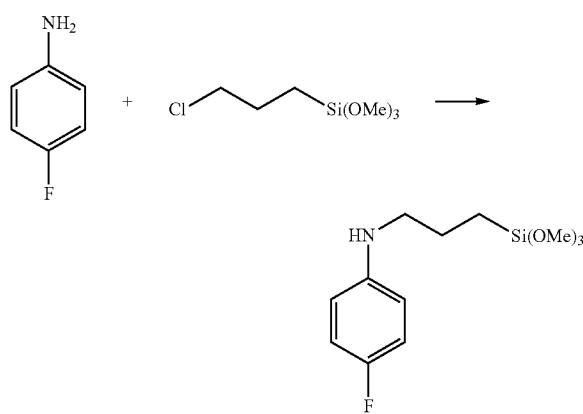

Chemical Formula 2

44.73 g (0.40 mol) of 4-fluoroaniline and 20.0 g (0.10 mol) of 3-chloropropyltrimethoxysilane were added to the 250 ml round-bottom flask, heated to 130° C., refluxed and agitated for 15 hours, and cooled to normal temperature. After 32.4 g of toluene was added thereto, the precipitate was removed by the filter, and the solvent was then removed from the filtrate in a vacuum. Thereafter, distillation under reduced pressure was performed to remove 4-fluoroaniline as the balance firstly discharged at about 120° C. and then obtain compound 1 of Chemical Formula 2 discharged at about 125° C. (11.3 g, yield: 41%). The measurement result of compound 1 by using $^1$H-NMR is as follows.

$^1$H NMR (500 MHz, CDCl$_3$, ppm): 6.86 (2H, t, ArH), 6.52 (2H, dd, ArH), 3.57 (9H, t, OCH$_3$), 3.07 (2H, t, CH$_2$), 1.80-1.68 (2H, m, CH$_2$), 0.71 (2H, t, CH$_2$).

Synthetic Example 2

Manufacturing of Compound 2

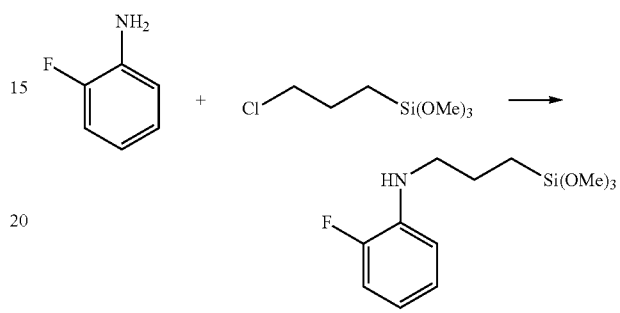

Chemical Formula 3

44.73 g (0.40 mol) of 2-fluoroaniline and 20.0 g (0.10 mol) of 3-chloropropyltrimethoxysilane were added to the 250 ml round-bottom flask, heated to 130° C., refluxed and agitated for 15 hours, and cooled to normal temperature. After 32.4 g of toluene was added thereto, the precipitate was removed by the filter, and the solvent was then removed from the filtrate in a vacuum. Thereafter, distillation under reduced pressure was performed to remove 2-fluoroaniline as the balance firstly discharged at about 120° C. and then obtain compound 2 of Chemical Formula 3 discharged at about 125° C. (10.2 g, yield: 37%). The measurement result of compound 2 by using $^1$H-NMR is as follows.

$^1$H NMR (500 MHz, CDCl$_3$, ppm): 6.98-6.88 (2H, t, ArH), 6.68-6.63 (2H, m, ArH), 6.58-6.53 (1H, m, ArH), 4.02 (1H, s, NH), 3.57 (9H, t, OCH$_3$), 3.15-3.09 (2H, m, CH$_2$), 1.76-1.68 (2H, m, CH$_2$), 0.71 (2H, t, CH$_2$).

Synthetic Example 3

Manufacturing of Compound 3

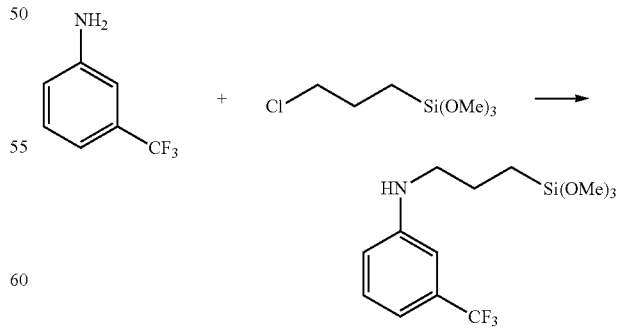

Chemical Formula 4

48.65 g (0.30 mol) of 3-(trifluoromethyl)aniline and 15.0 g (0.0755 mol) of 3-chloropropyltrimethoxysilane were added to the 250 ml round-bottom flask, heated to 130° C., refluxed and agitated for 15 hours, and cooled to normal temperature.

After 31.8 g of ethyl acetate was added thereto, the precipitate was removed by the filter, and the solvent was then removed from the filtrate in a vacuum. Thereafter, distillation under reduced pressure was performed to remove 3-(trifluoromethyl)aniline as the balance firstly discharged at about 100° C. and then obtain compound 3 of Chemical Formula 4 discharged at about 140° C. (6.0 g, yield: 24%). The measurement result of compound 3 by using $^1$H-NMR is as follows.

$^1$H NMR (500 MHz, CDCl$_3$, ppm): 7.22 (1H, t, ArH), 6.89 (1H, d, ArH), 6.78 (2H, s, ArH), 6.70 (1H, d, ArH), 4.02 (1H, s, NE), 3.57 (9H, t, OCH$_3$), 3.15 (2H, t, CH$_2$), 1.76-1.70 (2H, m, CH$_2$), 0.73 (2H, t, CH$_2$).

Example 1

Manufacturing of the Photosensitive Resin Composition 10 g of the alkali-soluble binder resin that was the copolymer of benzyl methacrylate/methaacrylic acid (BzMA/MAA) (molar ratio: 70/30, Mw: 10,000, acid value 115 KOH mg/g), 14 g of dipentaerythritol hexaacrylate that was the polymerizable compound having the ethylenically unsaturated bond, 0.06 g of BYK-331 that was the surfactant, 0.3 g of compound (1) manufactured as the adhesion aid in Synthetic Example 1 shown in the following Table 2, and 72.04 g of PGMEA that was the organic solvent were mixed by using the shaker for 3 hours to obtain the photosensitive resin composition solution.

Example 2

Manufacturing of the Photosensitive Resin Composition

The photosensitive resin composition was manufactured by the same method as Example 1, except that 0.3 g of compound (2) manufactured in Synthetic Example 2 shown in the following Table 2 was used as the adhesion aid.

Example 3

Manufacturing of the Photosensitive Resin Composition

The photosensitive resin composition was manufactured by the same method as Example 1, except that 0.3 g of compound (3) manufactured in Synthetic Example 3 shown in the following Table 2 was used as the adhesion aid.

Comparative Example 1

Manufacturing of the Photosensitive Resin Composition

The photosensitive resin composition was manufactured by the same method as Example 1, except that 0.3 g of comparative compound (1) shown in the following Table 2 was used as the adhesion aid.

Comparative Example 2

Manufacturing of the Photosensitive Resin Composition

The photosensitive resin composition was manufactured by the same method as Example 1, except that 0.3 g of comparative compound (2) shown in the following Table 2 was used as the adhesion aid.

TABLE 2

| Classification | Chemical Formula |
|---|---|
| Compound (1) | HN—(CH$_2$)$_3$—Si(OMe)$_3$ attached to para-F-phenyl |
| Compound (2) | HN—(CH$_2$)$_3$—Si(OMe)$_3$ attached to ortho-F-phenyl |
| Compound (3) | HN—(CH$_2$)$_3$—Si(OMe)$_3$ attached to meta-CF$_3$-phenyl |
| Comparative compound (1) | CH$_2$=C(CH$_3$)C(O)O—(CH$_2$)$_3$—Si(OMe)$_3$ (KBM-503) |
| Comparative compound (2) | HN—(CH$_2$)$_3$—Si(OMe)$_3$ attached to phenyl (Z-6883) |

Experimental Example 1

Measurement of Adhesion Strength

The photosensitive resin composition manufactured in Examples 1 to 3 and the Comparative Examples 1 and 2 was applied on glass by spin coating, and then subjected to preheating treatment at about 110° C. for 70 sec to form the uniform film having the thickness of about 3.7 μm.

After the film was exposed in an exposure intensity of 40 mJ/cm$^3$ under the high pressure mercury lamp by using a circular isolated pattern type of photomask having the diameter of 7 μm, the pattern was developed by the KOH alkali aqueous solution having the pH of 11.3 to 11.9 and washed by deionized water, and the results are described in the following Table 3. In Table 3, O means the case where the pattern remains due to excellent adhesion strength of the pattern during the developing, and X means the case where the pattern is completely removed by pattern elimination during the developing due to low adhesion strength of the pattern and the pattern does not remain.

Experimental Example 2

Measurement of Storage Stability

Viscosity was measured by the capillary viscometer immediately after the photosensitive resin composition of Examples 1 to 3 and Comparative Examples 1 and 2 was manufactured, and the viscosity was measured again by the same capillary viscometer after the composition was stored at normal temperature for one month to observe a change in viscosity. The result is shown in the following Table 3. O means the case where the viscosity after one month is changed by 3% or less without a large change as compared to the initial viscosity, and X means the case where the viscosity is increased to be changed by 3% or more.

TABLE 3

|  | Adhesion aid Compound | Photosensitive resin composition | |
|---|---|---|---|
|  |  | Adhesion strength | Storage stability |
| Example 1 | Compound (1) | ○ | ○ |
| Example 2 | Compound (2) | ○ | ○ |
| Example 3 | Compound (3) | ○ | ○ |
| Comparative Example 1 | Comparative compound (1) | Pattern elimination | ○ |
| Comparative Example 2 | Comparative compound (2) | ○ | X |

What is claimed is:

1. A silane-based compound represented by the following Chemical Formula 1:

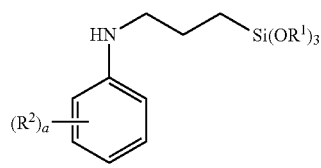

[Chemical Formula 1]

wherein,
R$^1$ is an alkyl group having 1 to 5 carbon atoms,
R$^2$ is each independently a halogen group or —C(R$^3$)$_3$,
R$^3$ is a halogen group, and
a is 1 to 5.

2. The silane-based compound of claim 1, wherein R$^1$ is a methyl group or an ethyl group, R$^2$ is F or CF$_3$, and a is 1 or 2.

3. The silane-based compound of claim 1, wherein Chemical Formula 1 is represented by any one of the following Chemical Formulas 2 to 9:

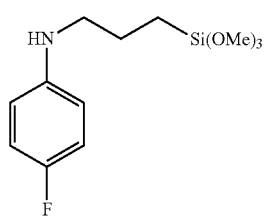

[Chemical Formula 2]

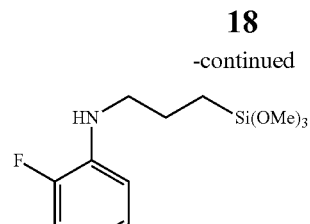

[Chemical Formula 3]

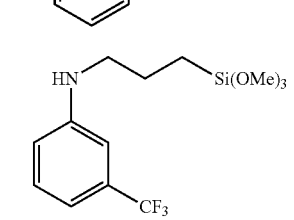

[Chemical Formula 4]

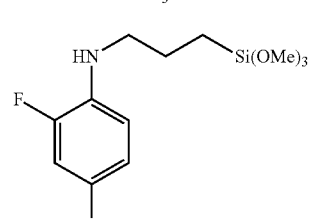

[Chemical Formula 5]

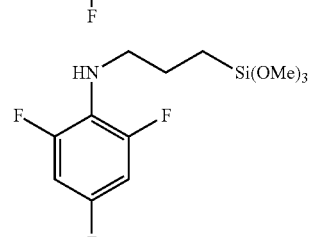

[Chemical Formula 6]

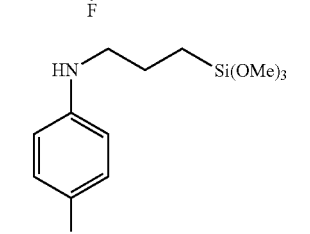

[Chemical Formula 7]

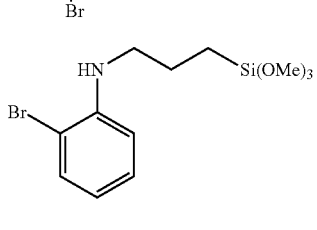

[Chemical Formula 8]

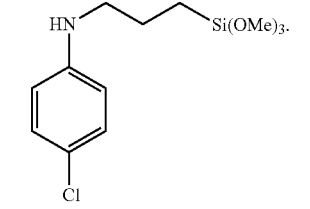

[Chemical Formula 9]

4. A photosensitive resin composition comprising:
the silane-based compound of claim 1;
a binder resin;
a polymerizable compound including an ethylenically unsaturated bond;
a photoactive compound; and
a solvent.

5. The photosensitive resin composition of claim 4, wherein a content of the silane-based compound is 0.01 to 5 wt % based on a total weight of the photosensitive resin composition.

6. The photosensitive resin composition of claim 4, wherein a content of the binder resin is 1 to 20 wt % based on a total weight of the photosensitive resin composition.

7. The photosensitive resin composition of claim 4, wherein a content of the polymerizable compound including the ethylenically unsaturated bond is 1 to 30 wt % based on a total weight of the photosensitive resin composition.

8. The photosensitive resin composition according to claim 4, wherein a content of the photoactive compound is 0.1 to 5 wt % based on a total weight of the photosensitive resin composition.

9. The photosensitive resin composition of claim 4, wherein a content of the solvent is 40 to 95 wt % based on a total weight of the photosensitive resin composition.

10. The photosensitive resin composition of claim 4, further comprising:
    a colorant.

11. The photosensitive resin composition of claim 10, wherein the colorant is included in a content of 1 to 20 wt % based on a total weight of the photosensitive resin composition.

12. The photosensitive resin composition of claim 4, further comprising:
    one or two or more additives selected from the group consisting of a curing accelerator, a thermal polymerization inhibitor, a dispersing agent, an antioxidant, a UV absorbent, a leveling agent, a photosensitizer, a plasticizer, an adhesion promoter, a filler, and a surfactant.

13. The photosensitive resin composition of claim 12, wherein the additives are each included in a content of 0.01 to 5 wt % based on a total weight of the photosensitive resin composition.

14. A photosensitive material manufactured by using the photosensitive resin composition of claim 4.

15. The photosensitive material of claim 14, wherein the photosensitive material is selected from the group consisting of a pigment dispersion type photosensitive material for manufacturing a color filter, a photosensitive material for forming a black matrix, a photosensitive material for forming an overcoat layer, a column spacer photosensitive material and a photosensitive material for a printed circuit board.

16. A color filter comprising:
    the photosensitive material of claim 14.

17. A method of manufacturing a photosensitive material, comprising:
    applying the photosensitive resin composition of claim 4 on a substrate; and
    exposing and developing the applied photosensitive resin composition.

18. An electronic device manufactured by using the photosensitive resin composition of claim 4.

* * * * *